US00PP10908P

United States Patent [19]

Bradford et al.

[11] Patent Number: Plant 10,908

[45] Date of Patent: Apr. 27, 1999

[54] NECTARINE TREE NAMED 'EARLY JUAN'

[76] Inventors: Lowell Glen Bradford, 12439 E. Savana Rd.; Norman G. Bradford, 11875 E. Savana Rd., both of Le Grand, Calif. 95333

[21] Appl. No.: 08/968,764

[22] Filed: Nov. 6, 1997

[51] Int. Cl.[6] ..... A01H 5/00

[52] U.S. Cl. ..... Plt./190

[58] Field of Search ..... Plt./40.1, 41.1, Plt./41.2, 190, 187, 191

[56] References Cited

U.S. PATENT DOCUMENTS

P.P. 5,438 4/1985 Bradford et al. ..... Plt./41

*Primary Examiner*—Howard J. Locker
*Assistant Examiner*—Ashwin Mehta

[57] ABSTRACT

The present invention relates to a nectarine tree, *Prunus persica*, and more particularly to a new and distinct variety broadly characterized by a large size, vigorous, self-fertile, productive and regular bearing tree. The fruit matures under the ecological conditions described approximately the third week in May, with first picking on May 13, 1997. The fruit is uniformly medium in size, acidic in flavor, globose to slightly oblong in shape, clingstone in type, medium firm in texture, and dark red in skin color. The variety was a first generation cross using 'Early Diamond' (U.S. Plant Pat. No. 5,438) nectarine as the selected seed parent and an unnamed seedling as the selected pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as 'Early Juan'. The present variety was developed by us in 1988 in a cultivated area of our experimental orchard at Bradford Farms near Le Grand, Calif. in Merced County (San Joaquin Valley). It was a first generation cross using 'Early Diamond' (U.S. Plant Pat. No. 5, 438) yellow flesh nectarine as the seed parent and an unnamed seedling as the selected pollen parent. Subsequent to origination of the present variety of nectarine tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The fruit produced by the present variety is most similar to its seed parent, the 'Early Diamond' (U.S. Plant Pat. No. 5, 438), by producing early maturing nectarines that are full red in skin color and yellow to the stone in flesh color, but is distinguished therefrom and an improvement thereon by producing fruit that ripens one week earlier, that is larger in size, that is less susceptible to split stones, that is clingstone instead of freestone, and that has a bitter kernel instead of sweet.

DRAWING

The accompanying photograph exhibits five whole fruits positioned to display the characteristics of the skin color and form, a sectioned fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif. and was developed at the state of firm eating ripe on May 19, 1997. All major color code designations are by reference to the Inter-Society Color Council, National Bureau of Standards. Common color names are also used occasionally.

Tree

Size: Large, currently maintained at a height of 12' [3.66 meters] in the plant breeding grounds using typical pruning practices.

Vigor: Vigorous, responding typically to irrigation and fertilization.

Growth: Spreading and dense.

Form: Vase formed.

Hardiness: Hardy, able to survive typical winter weather experienced in central California.

Production: Productive, thinning necessary.

Fertility: Self-fertile.

Bearing: Regular bearer, with no alternate bearing yet observed.

Trunk:

*Size*.—Medium, reaching a diameter of 7" [178 mm.] after nine growing seasons.

*Texture*.—Medium rough, with roughness increasing with age.

*Bark color*.—Grayish yellow brown [80. gy.yBr].

*Lenticels*.—Numerous. Color: Moderate brown [58. m. Br]. Average Size: ⅜" [9.5 mm.].

Branches:

*Size*.—Medium, typical of the species.

*Texture*.—Smooth on 1st year wood, increasing roughness with age.

*Color*.—1st Year wood topside: Grayish red [19. gy.R]. 1st Year wood underside: Light yellow green [119. l.YG]. Older wood: Strong yellowish brown [74. s.yBr].

*Lenticels*.—Numerous, small. Color: Light orange yellow [70. l.OY]. Average size: 1/16" [1.6 mm.].

Leaves:

*Size*.—Medium. Average length: 5¾" [146.1 mm.]. Average width: 1½" [38.1 mm.].

*Thickness*.—Medium.

*Form.*—Elliptical.
*Apex.*—Acuminate.
*Base.*—Acute.
*Surface.*—Smooth.
*Color.*—Dorsal surface: Moderate olive green [125. m.OlG]. Ventral surface: Moderate yellow green [120. m.YG].
*Margin.*—Finely serrate.
*Venation.*—Pinnately net veined.
*Petiole.*—Average length: 7/16" [11.1 mm.]. Average thickness: 1/16" [1.6 mm.]. Color: Moderate yellow green [120. m.YG].
*Stipules.*—Numerous, 2 per leaf, up to 6 per growing tip. Average length: 3/8" [9.5 mm.].
*Glands.*—Numbers: Mostly 2 per leaf. Position: Alternately positioned on petiole and base of blade. Size: Small. Form: Globose. Color: Billiant yellow green [116. brill.YG].

Flower buds:
*Hardiness.*—Hardy, with respect to central California winters.
*Diameter.*—Typically 3/8" [9.5 mm.] 1 week before bloom.
*Length.*—Typically 13/16" [20.6 mm.] 1 week before bloom.
*Form.*—Free.
*Surface.*—Pubescent.

Flowers:
*Blooming period.*—Early to medium as compared with other varieties.
*Onset of bloom.*—One percent on Feb. 20, 1998.
*Fragrance.*—Moderate, typical of the species.
*Type.*—Showy.
*Average diameter.*—1 7/8" [47.6 mm.].
*Color.*—Pale pink [7. p.Pk].

Fruit

Maturity when described: Firm eating ripe, May 19, 1997.
Date of first picking: May 13, 1997.
Date of last picking: May 25, 1997.
Size: Uniform, medium.
*Average diameter axially.*—2½" [63.5 mm.].
*Average transversely in suture plane.*—2 5/8" [66.7 mm.].
*Typical weight.*—5.7 ounces [162 grams].
Form: Globose to slightly oblong, uniform, slightly asymmetrical.
*Longitudinal section form.*—Round to oblong.
*Transverse section through diameter.*—Round.
Suture: A sharp groove close to the base becoming a shallow groove that continues to the apex, having a slight depression beyond the pistil point.
Ventral surface: Rounded, lipped throughout.
Lips: Slightly unequal.
Cavity: Flaring, circular.
Depth.—3/8" [9.5 mm.].
Breadth.—¾" [19.1 mm.].
Base: Rounded to slightly cuneate.
Apex: Rounded.
Pistil Point: Short in length, mostly depressed the suture.
Stem: Medium.
*Average length.*—3/8" [9.5 mm.].
*Average width.*—3/16" [4.8 mm.].
Skin:
*Thickness.*—Thin.
*Texture.*—Medium.
*Tenacity.*—Tenacious to flesh.
*Tendency to crack.*—None observed.
*Color.*—Dark red [16. d.R] blending over a strong red [12. s.R] background with very little freckling.

Flesh:
*Color.*—Brilliant Yellow [83. brill.Y] to the stone with no bleeding or streaking.
*Surface of pit cavity.*—Brilliant Yellow [83. brill.Y] fibers breaking when twisted away from the stone.
*Amygdalin.*—Moderate.
*Juice.*—Abundant, rich.
*Texture.*—Medium firm, crisp.
*Fibers.*—Abundant, fine.
*Ripens.*—Slightly earliest at the apex.
*Flavor.*—Acidic with medium sweetness.
*Aroma.*—Slight.
*Eating quality.*—Very good.

Stone

Type: Clingstone.
Form: Oval.
Base: Straight.
Apex: Acute.
Sides: Equal.
Surface: Irregularly furrowed toward the apex and pitted toward the base.
Ridges: Jagged toward the apex.
Color: Light yellowish brown [76. 1.yBr].
Pit wall: 3/16" [4.8 mm.] thick.
Tendency to split: Slight.
Kernel:
*Form.*—Oval.
*Taste.*—Bitter.
*Viable.*—Yes.
*Average Width.*—½" [12.7 mm.].
*Average length.*—¾" [19.1 mm.].
*Pellicle color.*—Grayish yellow [90. gy.Y].
*Amygdalin.*—Abundant.

Use

Market: Fresh and long distance shipping.
Keeping quality: Fruit quality observed to remain in good condition in excess of 14 days in cold room at 36° Fahrenheit [2° Celsius].
Resistance to insects: No unusual susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its seed parent, the 'Early Diamond' U.S. Plant Pat. No. 5,438), by producing early maturing nectarines that are full red in skin color and yellow to the stone in flesh color, but is distinguished therefrom and an improvement thereon by producing fruit that ripens one week earlier, that is larger in size, that is less susceptible to split stones, that is clingstone instead of freestone, and that has a bitter kernel instead of sweet.

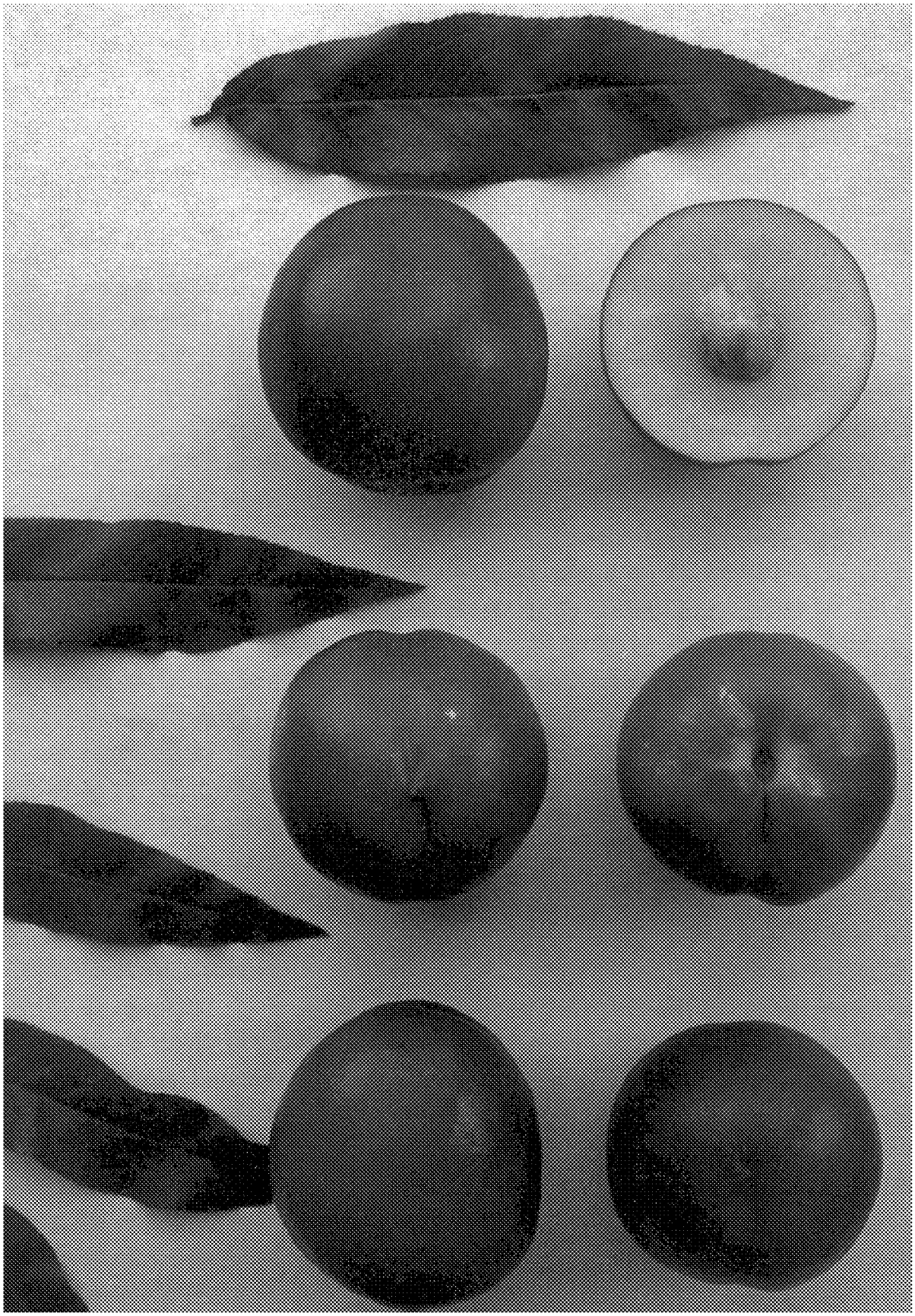

* * * * *